US012295750B2

(12) United States Patent
Myyrylainen et al.

(10) Patent No.: US 12,295,750 B2
(45) Date of Patent: May 13, 2025

(54) SKIN LIFTING FOR PHOTOPLETHYSMOGRAPHY

(71) Applicant: Nokia Technologies Oy, Espoo (FI)

(72) Inventors: Lea Myyrylainen, Espoo (FI); Helena Pohjonen, Espoo (FI)

(73) Assignee: Nokia Technologies Oy, Espoo (FI)

( * ) Notice: Subject to any disclaimer, the term of this patent is extended or adjusted under 35 U.S.C. 154(b) by 0 days.

(21) Appl. No.: 16/329,559

(22) PCT Filed: Oct. 6, 2017

(86) PCT No.: PCT/FI2017/050702
§ 371 (c)(1),
(2) Date: Feb. 28, 2019

(87) PCT Pub. No.: WO2018/069571
PCT Pub. Date: Apr. 19, 2018

(65) Prior Publication Data
US 2019/0216400 A1    Jul. 18, 2019

(30) Foreign Application Priority Data

Oct. 11, 2016    (EP) ..................................... 16193376

(51) Int. Cl.
*A61B 5/00* (2006.01)
*A61B 5/024* (2006.01)
*A61B 5/1455* (2006.01)

(52) U.S. Cl.
CPC .......... *A61B 5/6843* (2013.01); *A61B 5/0055* (2013.01); *A61B 5/02427* (2013.01); *A61B 5/14551* (2013.01); *A61B 5/6885* (2013.01); *A61B 2562/0238* (2013.01); *A61B 2562/0242* (2013.01)

(58) Field of Classification Search
CPC ... A61B 5/6843; A61B 5/6885; A61B 5/0055; A61B 5/14551; A61B 5/02427; A61B 2562/0242; A61B 2562/0238
See application file for complete search history.

(56) References Cited

U.S. PATENT DOCUMENTS

| | | | |
|---|---|---|---|
| 6,167,290 A | 12/2000 | Yang et al. | 600/322 |
| 7,641,614 B2* | 1/2010 | Asada | A61B 5/6826 600/500 |
| 2008/0041172 A1* | 2/2008 | Jaffe | G01N 1/24 73/863.83 |
| 2013/0085356 A1* | 4/2013 | Schlottau | A61B 5/6803 600/335 |
| 2014/0058227 A1* | 2/2014 | Yamanaka | G01N 21/64 600/316 |

(Continued)

FOREIGN PATENT DOCUMENTS

| | | |
|---|---|---|
| WO | WO 2007/015255 A2 | 2/2007 |
| WO | WO 2009/141755 A1 | 11/2009 |

*Primary Examiner* — Etsub D Berhanu
*Assistant Examiner* — Joseph A Tombers
(74) *Attorney, Agent, or Firm* — McCarter & English, LLP

(57) ABSTRACT

An apparatus, method and computer program are provided. The apparatus includes a light source; a light sensor configured to sense light signals emitted by the light source; and an actuator configured to lift a surface of skin tissue in order to create an optical path through the skin tissue from the light source to the light sensor, for transmissive photoplethysmography.

18 Claims, 5 Drawing Sheets

(56) References Cited

U.S. PATENT DOCUMENTS

Figure 1:
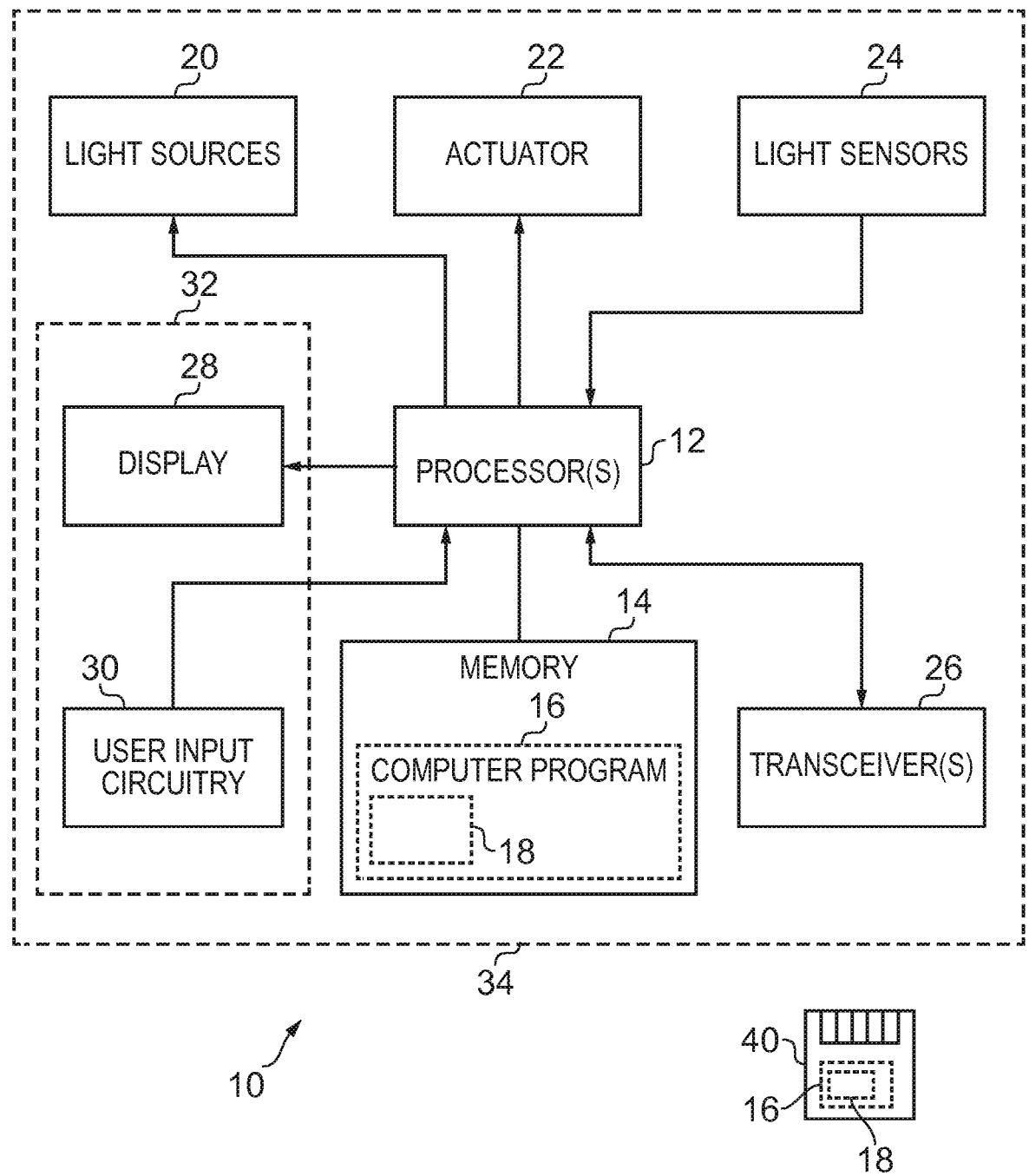

2017/0014040 A1\* 1/2017 Shim ................... A61B 5/002
2017/0119290 A1   5/2017 Cai et al.
2017/0347957 A1\* 12/2017 van den Ende ......... A61B 8/44
2019/0178764 A1\* 6/2019 Pelssers ................ A61B 5/442

\* cited by examiner

SKIN LIFTING FOR PHOTOPLETHYSMOGRAPHY

CROSS REFERENCE TO RELATED APPLICATION

This patent application is a U.S. National Stage application of International Patent Application Number PCT/FI2017/050702 filed Oct. 6, 2017, which is hereby incorporated by reference in its entirety, and claims priority to EP 16193376.7 filed Oct. 11, 2016.

TECHNOLOGICAL FIELD

Embodiments of the present invention relate to photoplethysmography. In particular, they relate to measurement of one or more physiological parameters such as heart rate (HR), heart rate variability (HRV) and/or peripheral capillary oxygen saturation ($SpO_2$) using photoplethysmography.

BACKGROUND

Photoplethysmography relates to performing volumetric measurement of an organ using optics. Pulse oximetry is a photoplethysmographic method of measuring oxygen saturation in blood.

A person's heart rate, heart rate variability and peripheral capillary oxygen saturation may be determined using such a method. In transmissive photoplethysmography, light signals are sensed by the light sensor after they have been emitted through tissue by the light source. In reflective photoplethysmography, light signals are sensed by the light sensor after being reflected by the tissue.

BRIEF SUMMARY

According to various, but not necessarily all, embodiments of the invention there is provided an apparatus, comprising: a photoplethysmography light source; a photoplethysmography light sensor configured to sense light signals emitted by the photoplethysmography light source; and an actuator configured to lift a surface of skin tissue in order to create an optical path through the skin tissue from the photoplethysmography light source to the photoplethysmography light sensor, for transmissive photoplethysmography.

According to various, but not necessarily all, embodiments of the invention there is provided a method, comprising: controlling, by at least one processor, lifting of a surface of skin tissue in order to create an optical path through the skin tissue from a photoplethysmography light source to a photoplethysmography light sensor, for transmissive photoplethysmography.

According to various, but not necessarily all, embodiments of the invention there is provided an apparatus, comprising: means for emitting light; means for sensing light; emitted by the means for emitting light; and means for lifting a surface of skin tissue in order to create an optical path through the skin tissue from the means for emitting light to the means for sensing light, for transmissive photoplethysmography.

According to various, but not necessarily all, embodiments of the invention there is provided an apparatus, comprising: at least one processor; and at least one memory storing computer program instructions that, when performed by the at least one processor, cause at least the following to be performed: controlling, by the at least one processor, lifting of a surface of skin tissue in order to create an optical path through the skin tissue from a photoplethysmography light source to a photoplethysmography light sensor, for transmissive photoplethysmography.

According to various, but not necessarily all, embodiments of the invention there is provided a computer program comprising computer program instructions that, when performed by the at least one processor, cause: controlling lifting of a surface of skin tissue in order to create an optical path through the skin tissue from a photoplethysmography light source to a photoplethysmography light sensor, for transmissive photoplethysmography.

According to various, but not necessarily all, embodiments of the invention there is provided examples as claimed in the appended claims.

BRIEF DESCRIPTION

Figure 2:
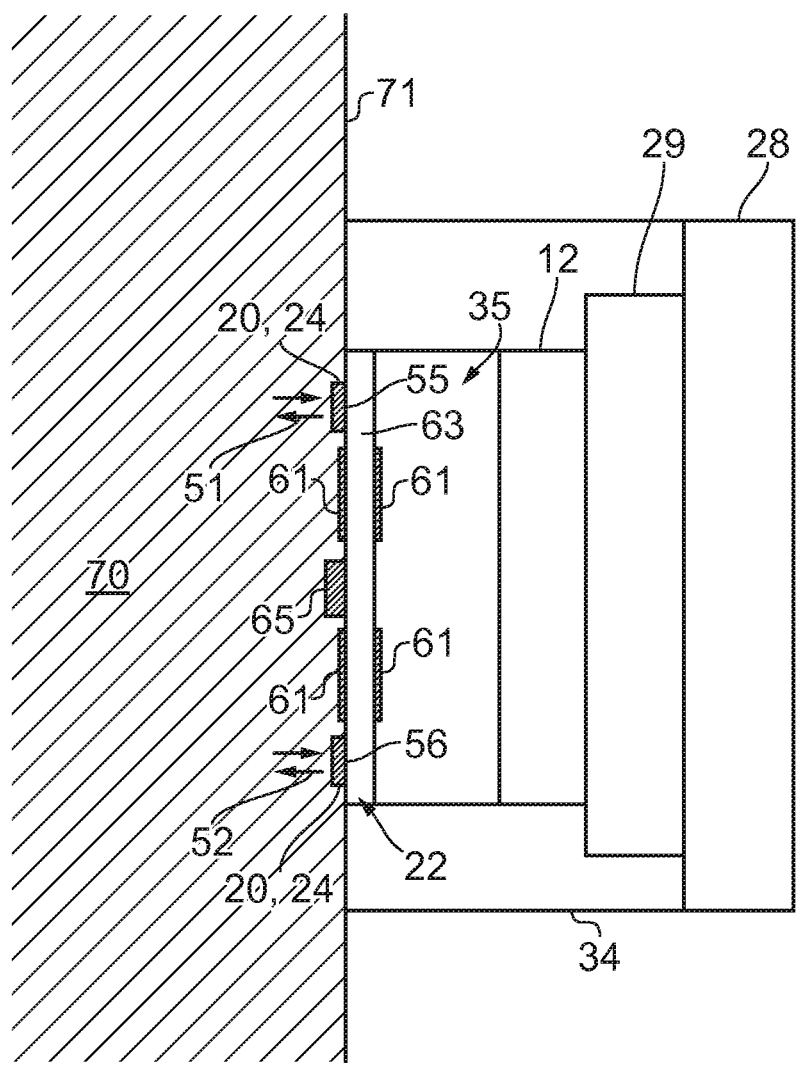
Figure 3:
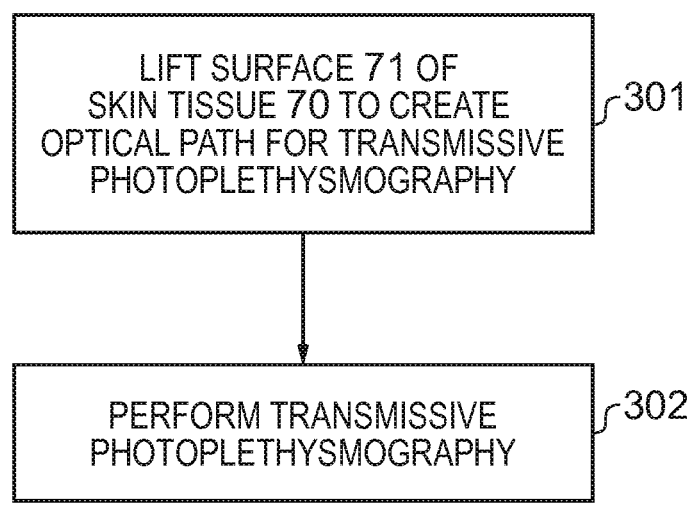
Figure 4:
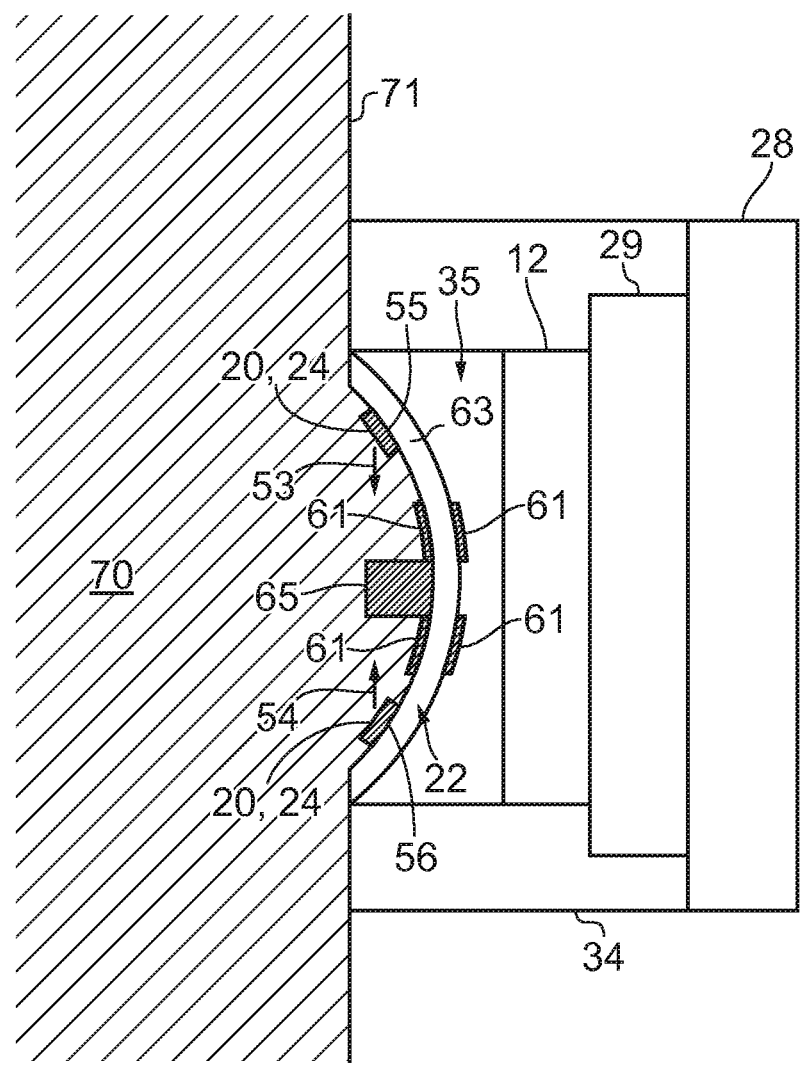
Figure 5:
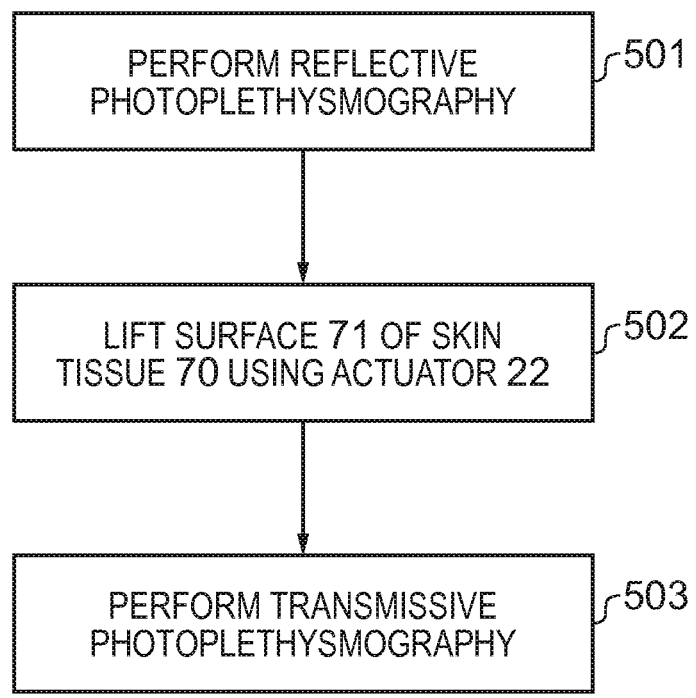

For a better understanding of various examples that are useful for understanding the detailed description, reference will now be made by way of example only to the accompanying drawings in which:

FIG. 1 illustrates a schematic of an apparatus;
FIG. 2 illustrates a schematic of the apparatus being worn by a person;
FIG. 3 illustrates a first flow chart of a method;
FIG. 4 illustrates a schematic of the apparatus being worn by a person when the actuator has lifted a surface of skin tissue; and
FIG. 5 illustrates a second flow chart of a method.

DETAILED DESCRIPTION

Embodiments of the invention relate to relate to photoplethysmography, and, in particular, measurement of one or more physiological parameters such as heart rate (HR), heart rate variability (HRV) and/or peripheral capillary oxygen saturation ($SpO_2$) using photoplethysmography.

A technical effect of embodiment of the invention is the provision of transmissive photoplethysmography without a need to position a photoplethysmography light source and a photoplethysmography light sensor on opposing faces of tissue. This technical effect is provided by actuator which lifts a surface of skin tissue in order to create an optical path through the skin from the photoplethysmography light source to the photoplethysmography light sensor, for transmissive photoplethysmography.

FIG. 1 illustrates a schematic of an apparatus 10. The apparatus comprises one or more processors 12, at least one memory 14, at least one photoplethysmography light source 20, at least one actuator 22, at least one photoplethysmography light sensor 24, at least one transceiver 26, at least one display 28 and user input circuitry 30.

The photoplethysmography light source(s) 20 may, for example, be one or more light emitting diodes (LEDs). The light source(s) 20 may, for example, be configured to emit visible and/or infrared light signals. The visible light signals may have a wavelength in the range 500-600 nanometers (green light) and/or a wavelength in the range 600-700 nanometers (red light). The processor 12 is configured to control the emission of light signals by the light source(s) 20.

The photoplethysmography light sensor(s) 24 may, for example, include one or more photodetectors and/or one or more image sensors, such as one or more charge-coupled devices (CCDs) and/or one or more complementary metal-oxide-semiconductor (CMOS) sensors. Each of the light sensors 24 is sensitive to light emitted by the light source(s) 20. The processor 12 is configured to receive inputs from the light sensor(s) 24 representing sensed light signals.

The processor 12 is configured to control the actuation of the actuator 22. An analogue to digital converter may be present between the processor 12 and the actuator 22 to convert digital control signals provided by the processor 12 into analogue electrical signals that are output to the actuator 22.

The actuator 22 is configured to lift a surface of skin tissue when the apparatus 10 is worn by a person and the actuator 22 is placed adjacent the surface of the skin tissue. The actuator 22 may sealingly attach to the surface of the skin tissue and lift the surface of the skin tissue by a suction effect. The actuator 22 may, for example, include an electro-active material, such as an electro-active polymer, which changes its shape and/or configuration in response to the application of an electrical signal to the electro-active material. In some implementations, the actuator 22 is an electro-active polymer pump.

The one or more transceivers 26 are configured to establish a communication link between the apparatus 10 and one or more other entities, such as a local device (for example, a mobile telephone or a computer) or a remote device (such as a remote server). The communication link might, for example, be a wired communication link such as a Universal Serial Bus (USB) link or a wireless communication link such as a Bluetooth link, an IEEE 802.11 link or a cellular link. The processor 12 is configured to provide outputs to and receive inputs from the transceiver(s) 26.

The one or more transceivers 28 provide the apparatus 10 with the ability to communicate with the other devices, enabling it to potentially form part of a system of devices that communicate together and/or part of a cloud-based health platform/service.

The display 28 is configured to display information to a wearer/user of the apparatus 10. The display 28 may, for example, be a liquid crystal display (LCD), an organic light emitting diode (OLED) display or a quantum dot (QD) display. The processor 12 is configured to control the display 28.

The user input circuitry 30 is configured to receive inputs from a user and provide corresponding inputs to the processor 12. The user input circuitry 30 may, for example, include mechanical input devices such as one or more keys or dials. At least part of the user input circuitry 30 might be combined with the display 28 in the form of a touch sensitive display 32.

The processor(s) 12 is/are described as a single item for ease of explanation in this document, but in practice multiple processors may be provided. The processor 12 may be a single core or multi-core processor.

The processor 12 is configured to read from and write to the memory 14. The processor 12 may also comprise an output interface via which data and/or commands are output by the processor 12 and an input interface via which data and/or commands are input to the processor 12.

The memory 14 stores a computer program 16 comprising computer program instructions (computer program code) 18 that controls the operation of the apparatus 10 when loaded into the processor 12. The computer program instructions 18, of the computer program 16, provide the logic and routines that enables the apparatus to perform at least some aspects of the methods illustrated in FIGS. 3 and 5. The processor 12 by reading the memory 14 is able to load and execute the computer program 16.

As illustrated in FIG. 1, the computer program 16 may arrive at the apparatus 12 via any suitable delivery mechanism 40. The delivery mechanism 40 may be, for example, a non-transitory computer-readable storage medium, a computer program product, a memory device, a record medium such as a compact disc read-only memory (CD-ROM) or digital versatile disc (DVD), an article of manufacture that tangibly embodies the computer program 16. The delivery mechanism may be a signal configured to reliably transfer the computer program 16. The apparatus 10 may propagate or transmit the computer program 16 as a computer data signal.

Although the memory 14 is illustrated as a single component/circuitry it may be implemented as one or more separate components/circuitry some or all of which may be integrated/removable and/or may provide permanent/semi-permanent/dynamic/cached storage.

The elements 12, 14, 20, 22, 24, 26, 28 and 30 are operationally coupled and any number or combination of intervening elements can exist (including no intervening elements). In the illustrated example, each of the elements 12, 14, 20, 22, 24, 26, 28 and 30 is housed at least partially within a housing 34.

FIG. 2 illustrates a schematic of the apparatus 10 being worn by a person. The apparatus 10 has been positioned adjacent to a surface 71 of skin tissue 70. In some examples, the apparatus 10 may include a band which holds the apparatus 10 in place against the surface 71 of the skin tissue 70. In other examples, the apparatus 10 might, for instance, be adhered in place on the surface 71 of the skin tissue 70.

In the FIG. 2 example, the display 28 is positioned on an outer surface of the apparatus 10 of the wearer, such that it can be viewed in use. A battery 29 is also present, which is positioned between the processor 12 and the display 28 in this example. Other electronics, such as an analogue to digital converter, may be positioned adjacent the processor 12.

The actuator 22 can be seen in FIG. 2 positioned adjacent to, and in contact with, the surface 71 of the skin tissue 70. In this example, the actuator 22 is an electro-active polymer pump which comprises a membrane 63, electrodes 61 and at least one resilient member/spring 65. The membrane 63 is formed from an electro-active polymer. The spring 65 is configured to urge the membrane 63 away from the surface 71 of the skin tissue 70.

In this example, the spring 65 is located in a central position on one surface/face of the membrane 63 and the electrodes 61 may be ring-shaped electrodes which surround the spring 65 on that surface. Electrodes 63 are also positioned on the other surface/face of the membrane 63.

The apparatus 10 is configured to sealingly attach to the surface 71 of the skin tissue 70, around a perimeter which surrounds the membrane 63. FIG. 2 illustrates a situation in which the processor 12 is not causing an electric signal to be applied to the electrodes 61 (that is, the actuator 22 is in its non-actuated state).

As explained above in relation to FIG. 1, the elements 12, 14, 20, 22, 24, 26, 28 and 30 are housed at least partially within a housing 34. The housing 34 defines an internal cavity 35 which enables the membrane 63 to move within the housing 34 when the actuator 22 is actuated. This is explained in further detail below.

The apparatus 10 illustrated in FIG. 2 includes at least one light source 20 and at least one light sensor 24 located in a first position 55 (on the membrane 63) and at least one light source 20 and at least one light sensor 24 located in a second position 56 (on the membrane 63). The first and second positions 55, 56 are different. In FIG. 2, each of the light sources 20 and light sensors 24 is located on the same surface of the membrane 63, adjacent to the electrodes 63. The electrodes 63 and at least some or all of the light sources 20 and light sensors 24 may be formed in the same integrated circuit.

FIG. 3 illustrates a flow chart according to a method according to embodiments of the invention. Initially, the apparatus 10 is applied to the surface 71 of the skin tissue 70 as illustrated in FIG. 2. Subsequently, at block 301 in FIG. 3, the processor 12 controls the actuator 22 to lift the surface 71 of the skin tissue 70 in order to create an optical path through the skin tissue 70 from a light source 20 to a light sensor 24, for transmissive photoplethysmography. That is, the processor 12 causes actuation of the actuator 22 which in turn causes the lifting of the surface 71 of the skin tissue 70.

FIG. 4 illustrates the actuator 22 in its actuated state. In actuating the actuator 22, the processor 12 causes an electrical signal to be applied to the electrodes 61 which creates an electrostatic force between the electrodes 61 on opposing faces of the membrane 63, bringing them closer together and squeezing the membrane 63. This causes the membrane 63 to expand in dimensions that are perpendicular to the applied electric field and weakens the membrane 63. The membrane 63 then deforms under the force applied by the spring 65. The internal cavity 35 in the housing 34 provides a volume into which the membrane 63 can move, as illustrated in FIG. 4.

The apparatus 10 is sealingly attached to the surface 71 of the skin tissue 70, around a perimeter which surrounds the membrane 63. Movement of the membrane 63 provides a suction effect, in which pressure/a force is applied to the surface 71 of the skin tissue 70 that causes the surface 71 of the skin tissue 70 to lift, as illustrated schematically in FIG. 4. The magnitude of the contact pressure/force applied to the surface 71 of the skin tissue 70 depends upon the extent to which the membrane 63 is deformed, which in turn depends upon the electrical signal applied to the electrodes 61. The processor 12 is therefore able to adjust the magnitude of the applied contact pressure by appropriately controlling the electrical signal that is applied to the electrodes 61. The electrical signal that is applied to the electrodes 61 at an instance in time determines the position (the extent of deformation) of the membrane 63. If the processor 12 causes the application of an electrical signal to the electrodes 61 to cease, the actuator 22 returns to its non-actuated state, as illustrated in FIG. 2.

It will be recognized by those skilled in the art that the term "lift" (as used in this document) does not necessarily refer to movement in a vertical dimension defined by the direction of the force of gravity, although it may do. It refers to the outwards movement of the surface 71 of the skin tissue 70 from its original, natural position.

After the surface 71 of the skin tissue 70 has been lifted, transmissive photoplethysmography is performed by the apparatus 10 at block 302 in FIG. 3 while the actuator 22 is in its actuated state using the newly created optical path(s) through the skin tissue 70. This may involve performing pulse oximetry. The processor 12 may, for example, perform blood flow analysis (such as capillary blood circulation analysis) by analysing the light signals sensed by the light sensors 24 to determine (quantify) at least one physiological parameter such as heart rate (HR), heart rate variability (HRV) and/or peripheral capillary oxygen saturation ($SpO_2$). Alternatively or additionally, the processor 12 may perform tissue analysis related to tissue flexibility, collagen, etc. using the light signals sensed by the light sensors 24.

The processor 12 may cause the determined physiological parameter(s) may be transmitted to another apparatus by controlling one or more of the transceivers 26 to transmit an appropriate signal to the other apparatus.

When the actuator 22 is in its actuated state, light emitted by the light source 20 located in the first position 55 travels along a new optical path through the skin tissue 70 that was created by movement of the membrane 63 and the surface 71 of the skin tissue 70, and is sensed by the light sensor 24 at the second position 56. The new optical path may also be created, at least in part, by a change in orientation of the light source 20 located in the first position 55 and/or a change in orientation of the light sensor 24 located in the second position 56 due to movement of the membrane 63 on which they reside.

Light emitted by the light source 20 located in the second position 56 travels along a new optical path through the skin tissue 70 that was created by movement of the membrane 63 and the surface 71 of the skin tissue 70, and is sensed by the light sensor 24 at the first position 55. The new optical path may also be created, at least in part, by a change in orientation of the light source 20 located in the second position 56 and/or a change in orientation of the light sensor 24 located in the first position 55 due to movement of the membrane 63 on which they reside.

The emission of light from the light source 20 located in the first position 55 is illustrated schematically by the arrow 53 in FIG. 4. The emission of light from the light source 20 located in the second position 56 is illustrated schematically by the arrow 53 in FIG. 4.

It will be apparent to those skilled in the art that it is not necessary for the apparatus 10 to comprise multiple light sources 20 and multiple light sensors 24 in order to perform transmissive photoplethysmography (and pulse oximetry) in the manner described above in relation to FIG. 3. A potential benefit of having multiple light sources 20 and multiple light sensors 24 will be described below in relation to FIG. 5.

The processor 12 analyses light signals emitted by the light sources 20 and sensed by the light sensors 24. The processor 12 may control the actuator 22 based, at least in part, on an analysis of the sensed light signals. The contact pressure applied to the surface 71 of the skin tissue 70 may have an effect on the quality of the light signal that is sensed by the light sensor(s) 24, and, by controlling the actuator 22 to adjust the contact pressure, the quality of the light signal being sensed can be optimised. The processor 12 may control the actuator 22 to optimise the sensed light signal in accordance with one or more quality metrics which might include, for instance, signal-to-noise ratio, amplitude and/or intensity.

The processor 12 may therefore operate in accordance with a feedback loop in which the light signal sensed by the light sensor(s) 24 is analysed over a period of time and the contact pressure applied to surface 71 of the skin tissue 70 is adjusted (increased and/or decreased) over that over of time to obtain an optimal reading. It has been found empirically that the application of a contact pressure increases the amplitude of the sensed light signal up to a given contact pressure, but further increases in the contact pressure can then cause the amplitude of the sensed light signal to decrease.

In some implementations, the apparatus 10 may further comprise a sensor for sensing the contact pressure/force applied to the surface 71 of the skin tissue 70 by the actuator 22. The sensor may, for example, be a strain gauge. The processor 12 may, for instance, obtain a reading from the sensor each time the contact pressure applied by the actuator 22 is changed (or increased). If the reading is indicative of the contact pressure/force exceeding a threshold, the processor 12 may control the actuator 22 to reduce the contact pressure in order to reduce or eliminate possible wearer discomfort.

If the light signal sensed by the light sensors 24 is weak (for instance, it has a property, such as amplitude or intensity, which is below a predetermined threshold), and the processor 12 has tried to optimise the sensed light signal in accordance with a quality metric, the processor 12 may control the one or more of the transceivers 26 to transmit an alert signal to another apparatus (such as a remote server, or a computer or a mobile device/telephone).

FIG. 5 illustrates a second flow chart of a method according to embodiments of the invention. The method illustrated in FIG. 5 differs from that illustrated in FIG. 3 in that at block 501 in FIG. 5, the apparatus 10 operates in reflective photoplethysmography mode and performs reflective photoplethysmography. This may involve performing pulse oximetry. The processor 12 may, for example, analyse the light signals sensed by the light sensors 24 to determine (quantify) at least one physiological parameter such as heart rate (HR), heart rate variability (HRV) and/or peripheral capillary oxygen saturation (SpO$_2$).

As previously explained, FIG. 2 illustrates a situation in which the apparatus 10 has been applied to the surface 71 of skin tissue 70 and the actuator 22 is in its non-actuated state, without any lifting of the surface 71 of the skin tissue 70. In order to perform reflective photoplethysmography, the processor 12 may control the light sources 20 to emit light, which is then reflected back to the light sensors 24 by the skin tissue 70.

Light emitted by the light source 20 at the first position 55 is reflected by the skin tissue 70 and sensed by the light sensor 24 at the first position 55, as illustrated by the arrows labelled with the reference numeral 51 in FIG. 2. Light emitted by the light source 20 at the second position 56 is reflected by the skin tissue 70 and sensed by the light sensor 24 at the second position 56, as illustrated by the arrows labelled with the reference numeral 52 in FIG. 2.

It may be quicker to make an initial measurement of a physiological parameter using reflective photoplethysmography and then switch to transmissive photoplethysmography, rather than begin using transmissive photoplethysmography.

At block 502 in FIG. 5, processor 12 switches the apparatus 10 from operating in reflective photoplethysmography mode to operating in transmissive photoplethysmography mode and controls the actuator 22 to lift the surface 71 of the skin tissue 70 in order to create an optical path through the skin tissue 70 from a light source 20 to a light sensor 24 for transmissive photoplethysmography. This is done in the same manner as that described above in relation to block 301 in FIG. 3.

In block 503 in FIG. 5, transmissive photoplethysmography is performed in the manner described above in relation to block 302 in FIG. 3.

In implementations having light sources 20 and light sensors 24 located at different positions (such as that described above where a light source 20 and a light sensor 24 are located at the first position 55 and a light source 20 and a light sensor 24 are located at the second position 56) light signals emitted by different light sources 20 may have different characteristics. For example, light emitted by the light source 20 in the first position 55 may be of a first wavelength (for example, green light) and light emitted by the light source 20 in the second position may be of a second, different, wavelength (for example red light). The light sensors 24 may be sensitive to (at least) both of those wavelengths of light. Alternatively or additionally, light emitted by the light source 20 in the first position 55 may be modulated differently from light emitted by the light source 20 in the second position.

This enables the processor 12 to determine whether reflective photoplethysmography or transmissive photoplethysmography is being performed. For example, if the processor 12 determines that the light sensor 24 located in the first position 55 is sensing light emitted by the light source 20 in the first position 55, it may determine that reflective photoplethysmography is being performed. If the processor 12 determines (alternatively or additionally) that the light sensor 24 located in the first position 55 is sensing light emitted by the light source 20 in the second position 56, it may determine that transmissive photoplethysmography is being performed. Sensed light emitted from different light sources 20 may be processed separately by the processor 12. In some implementations, the results of the separate processing may be combined (for example, to produce an average).

Machine learning may be employed by the processor 12 to determine whether reflective photoplethysmography or transmissive photoplethysmography provides better (for instance, more accurate or reliable) readings in particular circumstances and the processes performed by the processor 12 when obtaining readings may be adjusted accordingly.

A technical effect of embodiments of the invention described above is that both reflective photoplethysmography and transmissive photoplethysmography can be performed using the apparatus 10. Furthermore, the apparatus 10 can switch between performing reflective photoplethysmography and transmissive photoplethysmography without having to be repositioned to a different location on the wearer's body. It may also be possible to perform reflective photoplethysmography and transmissive photoplethysmography simultaneously.

References to 'computer-readable storage medium' or a 'computer', 'processor' etc. should be understood to encompass not only computers having different architectures such as single/multi-processor architectures and sequential (Von Neumann)/parallel architectures but also specialized circuits such as field-programmable gate arrays (FPGA), application specific circuits (ASIC), signal processing devices and other processing circuitry. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term 'circuitry' refers to all of the following:

(a) hardware-only circuit implementations (such as implementations in only analog and/or digital circuitry) and (b) to combinations of circuits and software (and/or firmware), such as (as applicable):

(i) to a combination of processor(s) or (ii) to portions of processor(s)/software (including digital signal processor(s)), software, and memory(ies) that work together to cause an apparatus, such as a mobile phone or server, to perform various functions and (c) to circuits, such as a microprocessor(s) or a portion of a microprocessor(s), that require software or firmware for operation, even if the software or firmware is not physically present.

This definition of 'circuitry' applies to all uses of this term in this application, including in any claims. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular claim element, a baseband integrated circuit or applications processor integrated circuit for a mobile phone or a similar integrated circuit in a server, a cellular network device, or other network device.

At least some of the blocks illustrated in FIGS. 3 and 5 may represent steps in a method and/or sections of code in the computer program 16. The illustration of a particular order to the blocks does not necessarily imply that there is a required or preferred order for the blocks and the order and arrangement of the block may be varied. Furthermore, it may be possible for some blocks to be omitted.

Where a structural feature has been described, it may be replaced by means for performing one or more of the functions of the structural feature whether that function or those functions are explicitly or implicitly described.

Although embodiments of the present invention have been described in the preceding paragraphs with reference to various examples, it should be appreciated that modifications to the examples given can be made without departing from the scope of the invention as claimed. For example, the (relative) positioning of the elements 20, 22, 24, 28, 29, 34, 35, 61, 63, 65 of the apparatus 10 might not necessarily be the same as that illustrated in FIGS. 2 and 4.

In the embodiments described above, at least one resilient member/spring 65 is provided to urge the membrane 63 away from the surface 71 of the skin tissue 70. In other embodiments, it may be possible to use an alternative biasing mechanism/member, such as a mere mass, depending on the orientation of the membrane 63 in use.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the applicant claims protection in respect of any patentable feature or combination of features hereinbefore referred to and/or shown in the drawings whether or not particular emphasis has been placed thereon.

We claim:

1. An apparatus, comprising:
a light source;
a light sensor to sense light signals emitted by the light source and that make it to the light sensor; and
an actuator comprising a membrane having a surface configured to be in contact with skin tissue in both a non-actuated state and an actuated state, the light source and the light sensor being located on the surface of the membrane, being configured to be in contact with a surface of the skin tissue in both the non-actuated state and the actuated state, and being on opposite sides of a central position of the membrane, wherein when in contact with the surface of the skin tissue, in the actuated state, the membrane is deformed and causes the skin tissue to be lifted by the deformed membrane of the actuator so that the light signals pass through a created optical path through the lifted skin tissue from the light source to the light sensor to enable performance of transmissive photoplethysmography using at least the light sensor.

2. The apparatus of claim 1, further comprising at least one processor to analyze the light signals emitted by the light source and sensed by the light sensor to perform the transmissive photoplethysmography.

3. The apparatus of claim 2, wherein the at least one processor controls the actuator based at least in part on an analysis of the sensed light signals.

4. The apparatus of claim 1, wherein:
the actuator causes the membrane to deform and to lift the skin tissue in the actuated state;
in the non-actuated state, the skin tissue is not lifted by the membrane; and
the apparatus further comprises a further light sensor positioned to sense the light signals emitted by the light source and reflected from the skin tissue for reflective photoplethysmography, the reflective photoplethysmography occurring when the actuator is in the non-actuated state.

5. The apparatus of claim 4, further comprising at least one processor that analyzes the light signals emitted by the light source and sensed by the light sensor, wherein the at least one processor analyzes the light signals emitted by the light source and sensed by the light sensor when operating in the actuated state for the transmissive photoplethysmography, and analyzes the light signals emitted by the light source and sensed by the further light sensor when operating in the non-actuated state for reflective photoplethysmography.

6. The apparatus of claim 1, wherein the apparatus is configured to sealingly attach to the surface of the skin tissue.

7. The apparatus of claim 1, further comprising a spring at the central position that urges the membrane away from the surface of the skin tissue to deform the membrane.

8. The apparatus of claim 7, wherein the membrane comprises multiple electrodes on opposing sides of the membrane, wherein in response to electrical signals being applied to the multiple electrodes, an electrostatic force is formed between the electrodes on the opposing sides of the membrane, bringing the multiple electrodes closer together and squeezing the membrane, which weakens the membrane, and the membrane deforms under force applied by the spring.

9. The apparatus of claim 8, wherein:
the actuator causes the membrane to deform and to lift the skin tissue in the actuated state to position the light source and the light sensor to perform the transmissive photoplethysmography through the created optical path;
in the non-actuated state, the skin tissue is not lifted by the membrane, and the light source and the light sensor are positioned to enable performance of reflective photoplethysmography; and
the apparatus further comprises one or more processors that cause the actuator to switch between the actuated state and the non-actuated state, to apply the electrical signals to the multiple electrodes in the actuated state, and to cause the electric signals to not be applied to the multiple electrodes in the non-actuated state.

10. The apparatus of claim 1, further comprising a housing defining an internal cavity that enables the membrane to move in order to lift the skin tissue.

11. The apparatus of claim 1, further comprising a sensor that senses pressure applied to the surface of the skin tissue by the actuator and further comprising one or more processors that operate so that the light signals sensed by the light sensor are analyzed over a period of time, and contact pressure applied to the surface of the skin tissue is adjusted over that period of time to obtain a reading.

12. The apparatus of claim 1, wherein the actuator comprises an electro-active polymer pump.

13. The apparatus of claim 1, wherein the apparatus is a wearable device.

14. The apparatus of claim 1, wherein:
the actuator causes the membrane to deform and to lift the skin tissue in the actuated state to position the light source and the light sensor to perform the transmissive photoplethysmography through the created optical path; and
in the non-actuated state, the skin tissue is not lifted by the membrane, and the light source and the light sensor are positioned to enable performance of reflective photoplethysmography.

15. The apparatus of claim 14, further comprising one or more processors that cause the actuator to switch between the actuated state and the non-actuated state, wherein in the actuated state, the one or more processors analyze the light signals emitted by the light source and sensed by the light sensor using transmissive photoplethysmography, and when in the non-actuated state, the one or more processors analyze the light signals emitted by the light source and sensed by the light sensor using reflective photoplethysmography.

16. The apparatus of claim 1, wherein:
the actuator causes the membrane to deform and to lift the skin tissue in the actuated state;
in the non-actuated state, the skin tissue is not lifted by the membrane; and
the created optical path is created by movement of the membrane from the non-actuated state to the actuated state.

17. A method performed on an apparatus comprising a light source and a light sensor to sense light signals emitted by the light source and that make it to the light sensor, the method comprising:
controlling, in the apparatus, an actuator comprising a membrane having a surface in contact with skin tissue in both a non-actuated state and an actuated state, the light source and the light sensor being located on the surface of the membrane, being in contact with a surface of the skin tissue in both the non-actuated state and the actuated state, and being on opposite sides of a central position of the membrane, wherein the controlling causes the membrane in the actuated state to be deformed and causes the skin tissue to be lifted by the deformed membrane of the actuator so that the light signals pass through a created optical path through the lifted skin tissue from the light source to the light sensor; and
analyzing the light signals emitted by the light source and sensed by the light sensor to perform transmissive photoplethysmography.

18. A non-transitory computer-readable storage medium encoded with a computer program comprising computer program instructions that, when performed by at least one processor, cause an apparatus comprising a light source and a light sensor to sense light signals emitted by the light source and that make it to the light sensor to:
control, in the apparatus, an actuator comprising a membrane having a surface in contact with skin tissue in both a non-actuated state and an actuated state, the light source and the light sensor being located on the surface of the membrane, being in contact with a surface of the skin tissue in both the non-actuated state and the actuated state, and being on opposite sides of a central position of the membrane, wherein the controlling causes the membrane in the actuated state to be deformed and causes the skin tissue to be lifted by the deformed membrane of the actuator so that the light signals pass through a created optical path through the lifted skin tissue from the light source to the light sensor; and
analyze the light signals emitted by the light source and sensed by the light sensor to perform transmissive photoplethysmography.

* * * * *